United States Patent [19]
Johnson et al.

[11] Patent Number: 5,891,030
[45] Date of Patent: Apr. 6, 1999

[54] SYSTEM FOR TWO DIMENSIONAL AND THREE DIMENSIONAL IMAGING OF TUBULAR STRUCTURES IN THE HUMAN BODY

[75] Inventors: Charles Daniel Johnson; Amy Kiyo Hara; Judd Evon Reed, all of Rochester, Minn.

[73] Assignee: Mayo Foundation for Medical Education and Research, Rochester, Minn.

[21] Appl. No.: 787,286

[22] Filed: Jan. 24, 1997

[51] Int. Cl.$^6$ ..................................................... A61B 05/00
[52] U.S. Cl. ......................... 600/407; 382/128; 128/920
[58] Field of Search ................................... 600/407, 416; 378/66; 382/128, 131, 154, 285, 293, 294, 307, 302; 128/920, 922

[56] References Cited

U.S. PATENT DOCUMENTS

| | | |
|---|---|---|
| 4,630,203 | 12/1986 | Szirtes . |
| 4,939,646 | 7/1990 | Essinger et al. . |
| 5,170,170 | 12/1992 | Soumekh . |
| 5,178,150 | 1/1993 | Silverstein . |
| 5,323,111 | 6/1994 | Suzuki . |
| 5,361,763 | 11/1994 | Kao et al. . |
| 5,368,033 | 11/1994 | Moshfeghi . |
| 5,458,111 | 10/1995 | Coin . |
| 5,699,799 | 12/1997 | Xu et al. . |

OTHER PUBLICATIONS

Dachman, Abraham H., James Lieberman, Robert B. Osnis, Shiuh–Yung J. Chen, Kenneth R. Hoffmann, Chin–Tu Chen, Geraldine M. Newmark and James McGill, "Small Simulated Polyps in Pig Colon: Sensitivity of CT Virtual Colography", *Radiology*, v. 203, pp. 427–430 May 1997.

Erickson, Deborah, "Colonic Gold: Simulated flights through patients'bowels may one day permit widespread screening without scoping", *Physicians Weekly*, Jun. 26, 1995.

GE Medical Systems, "Advantage Windows: Diagnostic Workstation" (brochure). before filing date, Jan. 27, 1997.

Haney, Daniel Q., "Simpler Colon Test Reported, X–rays: computers are linked for inside view without tube", *The Plain Dealer*, p. 8–A, Mar. 28, 1995.

Hara, A.K., C.D. Johnson, J.E. Reed, D.A. Ahlquist, H. Nelson, R.L. Ehman and W.S. Harmsen, "Reducing Data Size and Radiation Dose for CT Colonography", *American Journal of Radiology*, v. 168, pp. 1181–1184, May 1997.

Hara, Amy K., C. Daniel Johnson, Judd E. Reed, Richard L. Ehman, and Duane M. Ilstrup, "Colorectal Polyp Detection Using Computed Tomographic Colography: 2D Versus 3D Techniques", *Radiology*, v. 200, No. 1 pp. 49–54, Jun. 1996.

Hara, Amy K., C. Daniel Johnson, Judd E. Reed, David A. Ahlquist, Heidi Nelson, Richard L. Ehman, Cynthia H. McCollough, and Duane M. Ilstrup, "Detection of Colorectal Polyps by Computed Tomographic Colography: Feasibility of a Novel Technique", *Gastroenterology*, v. 110, pp. 284–290. Before Filing Date, 1996.

(List continued on next page.)

*Primary Examiner*—Marvin M. Lateef
*Assistant Examiner*—Shawna J. Shaw
*Attorney, Agent, or Firm*—Faegre & Benson LLP

[57] ABSTRACT

A system, method, and article of manufacture for imaging tubular structures of the human body, such as the digestive tract of a living person, with a medical imaging device such as a computed tomography (CT) scanner and a computer workstation. The CT scanner is used to generate cross-sectional axial images of a human colon which are then transferred to the computer workstation. A colon midline is defined which follows the colon lumen. The computer workstation supports colon midline definition by generating and displaying reformatted cross-sectional images, volume rendered scouts, and interluminal views. Semi-automatic midline defining tools are also included. After the midline is defined, a montage of images is displayed for diagnostic purposes. The images include axial sections, transluminal cross section, and intraluminal volume rendered images.

58 Claims, 10 Drawing Sheets

OTHER PUBLICATIONS

Ogura, T., K. Koizumi, S. Kai and M. Maruyama, Three–Dimensional CT Colonscopy: Comparison with Colonscopy and Barium Enema Examination, Scientific Exhibits, Radiology of North America, Nov. 1995.

Reed, Judd E, Amy K. Hara and C. Daniel Johnson, "Interpretation of Image Sets Containing Convoluted Tubular Structures Via Transluminal Sections and Steerable Intraluminal Perspective Views", Proceedings of International Society for Optical Engineering, v. 710, pp. 1109–1019, Feb. 1996.

Riotto, Mark,"Virtual Reality Provides a Closer Look at Colon", *Radiology Today*, p. 11, Jul. 1994.

Rubin, Geoffrey D., Christopher F. Beaulieu, Vincent Argiro, Helmut Ringl, Alexander M. Norbash, John F. Feller, Michael D. Dake, R. Brooke Jeffrey, and Sandy Napel, "Perspective Volume Rendering of CT and MR Images: Applications for Endoscopic Imaging", *Radiology*, v. 199, pp. 321–330. Before filing date, 1996.

Vining, David J., Barbara Vanderwerken, Elizabeth Teigen, Wallace Wu, David Gelfand, "Update of Virtual Colonoscopy" *The Society of Gastrointestinal Radiologists*, Twenty–Fifth Annual Meeting and Postgraduate Course, Mar. 24–29, 1996.

Vining, D.J. K. Lui, P.F. Helmer,and D. Ahn, "Principles of Virtual Reality Imaging", Scientific Exhibits, Radiology Society of North America, Nov. 1995.

Vining, David J., and David W. Gelfand, "Noninvasive Colonoscopy Using Helical CT Scanning, 3D Reconstruction, and Virtual Reality", *Society of Radiologists*, Feb. 1994.

Vining, D.J., and E.L. Teigen, "Experience with Virtual Colonoscopy in 20 Patients", Scientific Exhibits, Radiology Society of North America, Nov. 1995.

Vining, D.J., R.Y. Shifrin, E.K. Grishaw, K. Liu and D.W. Gelfand, "Virtual Colonscopy", *Radiology Society of North America (RSNA)* v. 193, p. 446. Before Filing Date, 1994.

Vining, David J., Ronald J. Zagoria, Kun Liu and David Stelts, "CT Cystoscopy: An Innovation in Bladder Imaging", *American Journal of Radiology*, v. 166 pp. 409–410, Aug. 2, 1995.

Woodhouse, C.E. and J.L. Friedman, "In Vitro Air–Contrast– enhanced Spiral 3D CT (Virtual Coloscopy) Appearance of Colonic Lesions", Scientific Exhibits, Radiology Society of North America, Nov. 1995.

Wang, Ge and Michael W. Vannier, "GI Tract Unraveling by Spiral CT", *SPIE*, vol. 2434 pp. 307–315. Before filing date, Jan. 27, 1997.

Zeiberg, Andrew S., Paul M. Silverman, Roy B. Sessions, Thomas R. Troost, William J. Davros, and Robert K. Zeman, "Helical (Spiral) CT of the Upper Airway with Three–Dimensional Imaging: Technique and Clinical Assessment", *American Roentgen Ray Society*, v. 166, pp. 293–299, Feb. 1996.

FIG. 8

Review COLON version 2.3 ( DATE ):5_PT  RESTORE DEFAULTS  FINISH

DISTANCE ALONG: 435.0 mm.

REFERENCE VIEWS  AXIAL  TOMO  AIR SCOUTS

SHOW TRANSIENT: BOTH  RENDERINGS  SECTIONS  NEITHER

3D FOV (deg) 110  30 ———— 180
Depth of View 90  1 — 750
LO 3D Thres. 500 ———— -1000 / 1000
HI 3D Thres. -750 -1000 ———— 1000
Render Quality 1  12
Burrow depth *10 10  0 — 100
Step length *10 50  1 —— 151
WIN. WIDTH 640  1 ———— 2048
WIN. LEVEL -64  -1000 ———— 1047

( 2000:-200 )  ( 800:-200 )  ( 1000:-200 )  ( 400:40 )

SYSTEM FOR TWO DIMENSIONAL AND THREE DIMENSIONAL IMAGING OF TUBULAR STRUCTURES IN THE HUMAN BODY

FIELD OF THE INVENTION

The present invention generally relates to anatomical modeling of the human body with a computer, and more particularly to a computerized system for analyzing tubular structures of the human body such as the digestive tract of a living person for detecting colorectal polyps.

BACKGROUND OF THE INVENTION

In industrialized nations, colorectal cancer is the second leading cause of deaths from malignancy. In the United States, almost 150,000 people are found to have colon cancer annually and it causes approximately 60,000 deaths annually. Only lung cancer causes more deaths. Colon cancers are preventable because they usually begin as benign polyps which grow slowly for five to ten years before becoming cancerous. If these polyps are detected and removed, the risk of developing colon cancer is greatly reduced.

Unfortunately, widespread colorectal screening and preventive efforts are hampered by several practical impediments, including limited resources, methodologic inadequacies, and poor patient acceptance leading to poor compliance. In addition, a fecal occult blood test (FOBT) fails to detect the majority of cancers and pre cancerous polyps. Since sigmoidoscopy only examines a portion of the colon, it also misses many polyps. The accuracy of barium enema varies among centers and is therefore not always reliable.

Therefore, there is a need for a new test which can be used to screen for pre cancerous colon polyps. Like all screening tests, this new test must be relatively inexpensive, minimally invasive, and highly specific.

A technique using helical computed tomography (CT) to create computer simulated intraluminal flights through the colon was proposed as a novel approach for detecting colorectal neoplasms by Vining D J, Shifrin R Y, Grishaw E K, Liu K, Gelfand D W, *Virtual colonoscopy* (*Abst*), Radiology Scientific Prgm 1994; 193(P):446. This technique was first described by Vining et al. in an earlier abstract by Vining D J, Gelfand DW, *Noninvasive colonoscopy using helical CT scanning, 3D reconstruction, and virtual reality* (*Abst*), SGR Scientific Program, 1994. This technique, referred to as "virtual colonoscopy", requires a cleansed colon insufflated with air, a helical CT scan of approximately 30 seconds, and specialized three-dimensional (3D) imaging software to extract and display the mucosal surface. The resulting endoluminal images generated by the CT scan are displayed to a medical practitioner for diagnostic purposes.

The technique of reformatting 2D cross sections perpendicular to the colon midline is also described in U.S. Pat. No. 5,458,111, issued Oct. 17, 1995 to Coin. However, direct interpretation of the cross-sectional images is difficult because a scan of the colon consists of several hundred axial tomograms. Without advanced image manipulation tools, interpretation of the colon's complex three dimensional shape from these cross sections alone is very difficult for a medical practitioner.

One approach to improve accuracy involves production of reformatted 2D images at cross sections and orthogonal angles to the colon midline. These reformatted 2D images can provide complimentary diagnostic information when viewed with corresponding intraluminal 3D images. Exam efficiency can be improved with innovative 3D rendering techniques that allow fast, interactive evaluation on low priced computer hardware.

Therefore, there is a need for new techniques which provide efficient and accurate evaluation of the colon using helical CT data. There is a need for displaying coronal, sagittal, and axial views of the colon. There is also a need for displaying a three dimensional image of the colon. There is a further need for displaying an unfolded or open view of the colon.

SUMMARY OF THE INVENTION

The present invention provides a system, method, and article of manufacture for imaging tubular structures of the human body, such as the digestive tract of a living person, with a medical imaging device such as a computed tomography (CT) scanner and a computer workstation. The CT scanner is used to generate cross-sectional axial images of a human colon which are then transferred to the computer workstation. A colon midline is defined which follows the colon lumen. The computer workstation supports colon midline definition by generating and displaying reformatted cross-sectional images, volume rendered scouts, and interluminal views. Semi-automatic midline defining tools are also included. After the midline is defined, a montage of images is displayed for diagnostic purposes. The images include axial sections, transluminal cross section, and intraluminal volume rendered images.

Semiautomatic methods are used to delineate the three dimensional shape of the colon by identifying its approximate midline. This is supported by the display of coronal, sagittal, and axial views as well as an off-axis plane orthogonal to the midline. Straightened curved sections along the midline and a rendered view from the end of the midline are also displayed. Editing the midline in any of these views causes the other views to update accordingly. After the midline is traced, data are extracted so the colon can be examined efficiently.

A medical practitioner, such as a radiologist, examines the colon by moving the view point along the delineated midline. Three orthogonal off-axis cross sections, volume rendered extraluminal scouts or the raw axial 2D images, and a high resolution perspective rendering of the colon's inner surface are all displayed. The perspective views can be re-oriented in any direction. A rotatable longitudinal sectioning along the colon's midline is also displayed. This view, showing the entire length of the colon, enhances both navigation of the path forward or backward along the 3D images and interpretation of the 3D images.

Empirical research shows that the simultaneous display of cross-sectional and rendered views enhances a diagnostic interpretation more than either cross-sectional or intra luminal views alone. Volume rendering is performed by custom algorithms that use pre-computation of texture and other techniques to achieve interactive performance on moderately priced workstations. These greatly reduce the number of computations required to generate a ray traced image, which makes volume rendering possible with computational requirements similar to those of surface rendering.

Two views of the three dimensional images are displayed to the observer. The first view is a forward intraluminal view which encompasses a view of the colon from the view point looking away from a terminating location of the colon, such as the anal verge. The second view is a backward intraluminal view which encompasses a view of the colon from the view point looking toward a terminating location of the colon, such as the anal verge. Displaying both views makes it less likely that a feature of interest will be obscured due to the topology of the colon.

By pointing the cursor and simultaneously pressing a key, an observer can move the view point off the previously defined midline, and all images, including 2D reformatted images, 3D intraluminal images, and the 2D axial image are updated to views corresponding to the designated position. A fiducial mark on each of the images identifies the new position. The observer can randomly move the view point by using the pointing device, or return to the nearest point on the predetermined midline.

To denote orientation and location, two extraluminal renderings of the air-filled colon are displayed in axial and coronal orientations to assist the observer in determining location and orientation.

To assist in the diagnosis, an unfolded or opened view of the colon is also displayed to the observer. The opened view of the colon corresponds to a view of the entire colon as if it had been physically divided and opened for inspection.

BRIEF DESCRIPTION OF THE DRAWINGS

FIG. 8 is a screen display of a parameter adjustment window compatible with the present invention.

DETAILED DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural changes may be made without departing from the scope of the present invention.
GLOSSARY The following terms and phrases are used throughout the application.

1. Computed tomographic colonography (CTC). A technique combining helical or volumetric CT imaging of the colon with imaging software to produce reformatted 2D and 3D images of the colon.
2. Reformatted 2D images. Images which are oriented at cross section and two orthogonal angles to the colon midline.
3. 3D intraluminal image. An image which simulates an endoscopic view of the colon. The outside of the colon is not visualized.
4. 2D axial image. The original image produced by the helical or volumetric CT scanner before any image post-processing is performed.
5. Straightened colon/continuous orthogonal image. Images which are oriented at a cross section in the volume image of the straightened colon which correspond to a convoluted ribbon bisecting the colon along its axis.
6. 3D extraluminal images. Images which represent as 3D extraluminal rendering of the entire colon in axial, sagittal and coronal orientations.
7. Raw 2D images. Transaxial non-reformatted images generated by the CT scanner.

DETAILED DESCRIPTION

For the purpose of illustrating the best mode of practicing the present invention, this description describes the process of analyzing the colon of a living human patient. It will be recognized that the present invention can enhance the assessment of any tubular structure of the human body where intraluminal and transluminal views are desirable. By way of example, the present invention has been used to evaluate the trachea and bronchial tree, the bowel, and other vascular structures such as the aorta. One of ordinary skill in the art will recognize that other organs and structures of the human body in addition to those listed above, such as the heart, stomach, or bladder, may be analyzed with the present invention without loss of generality.

Figure 1:
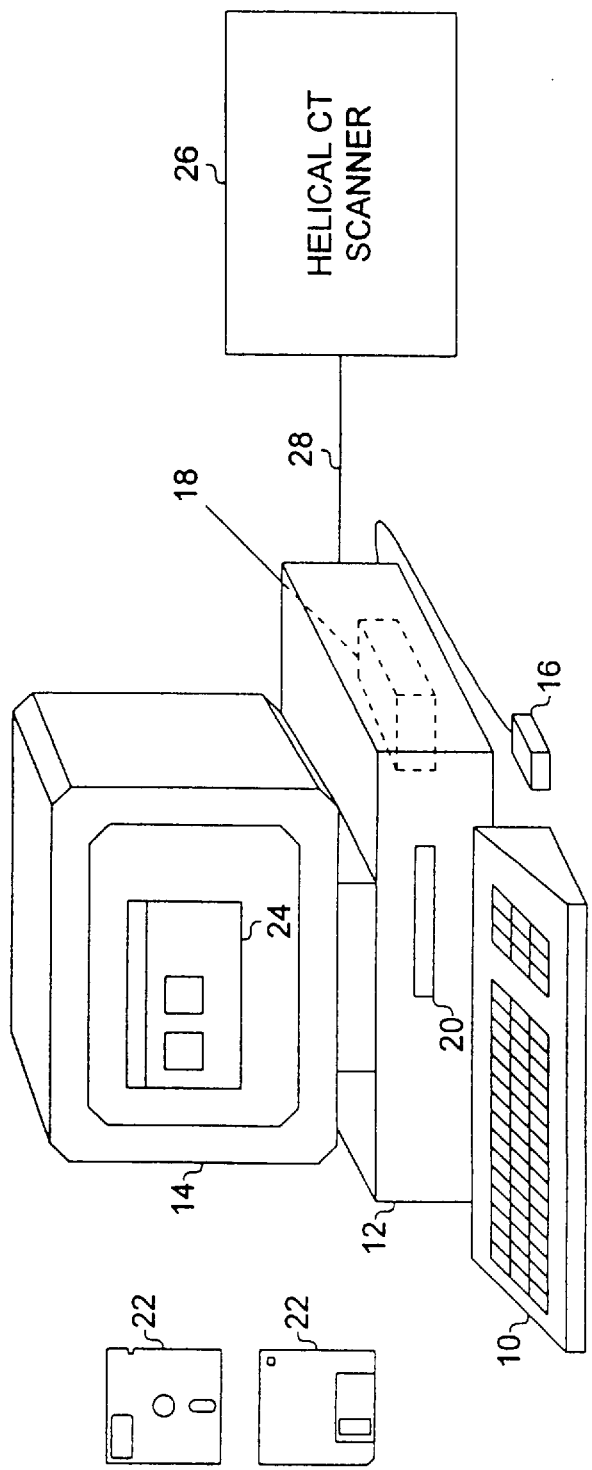
FIG. 1 is a perspective view of the components of a system for imaging a human body with a medical imaging device compatible with the present invention.

FIG. 1 shows the components of a preferred medical imaging system that may be used with the present invention. The system includes a workstation typically having a keyboard 10 by which a user may input data into the system, a computer chassis 12 which holds electrical processing components and a memory 18. The computer 12 also contains a removable storage device 20 by which removable media 22, typically floppy disks, magnetic tapes, or removable fixed disks, may be used to provide information to the computer 12. The computer 12 could also be coupled to other I/O devices, including a local area network (LAN) or wide area network (WAN) via interface cable 19. The system further contains a screen display 14 by which information 24 is displayed to the user, and a pointing device 16, typically a mouse. The computer components are logically connected to each other via internal system bus within the computer, which is further connected to a helical or volumetric CT scanner 26 via an external data bus 28. The present invention includes a preprogrammed set of instructions which are stored in the memory 18 and processed by one or more processing units within the computer 12.

Figure 2:
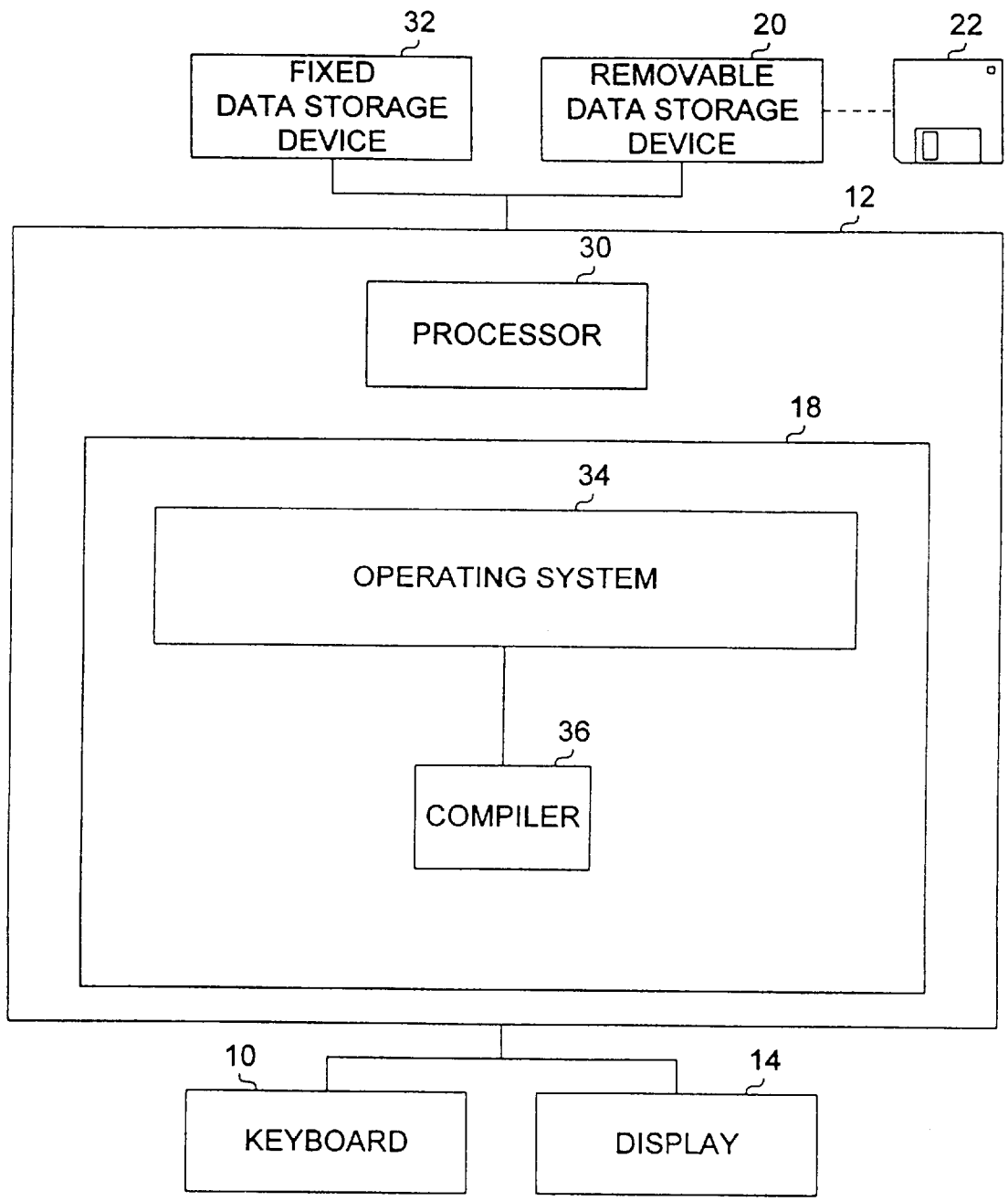
FIG. 2 is a block diagram illustrating an exemplary hardware environment used to implement a preferred embodiment of the invention.

FIG. 2 is a block diagram illustrating an exemplary hardware environment used to implement the preferred embodiment of the invention. In the exemplary hardware and software environment, the computer 12 may include, inter alia, a processor 30, memory 18, keyboard 10, screen display 14, as well as fixed and/or removable data storage devices and their associated media 20, 22, and 32. Those skilled in the art will recognize that any combination of the above components, or any number of different components, peripherals, and other devices, may be used with the computer 12.

The present invention is generally implemented using a compiler program, and a linker program, each of which executes under the control of an operating system 34, such as OS/2, Windows, AIX, UNIX, DOS, etc. For purposes of simplification, the compiler program and linker program will be collectively referred to herein as a compiler 36. Those skilled in the art will recognize that the compiler 36 can conform to many programming language conventions without departing from the scope of the present invention. A graphical user interface (GUI) 38 executes under the control the operating system 34 to provide text and graphics information on the screen display 14.

Those skilled in the art will recognize many modifications may be made to this configuration without departing from the scope of the present invention.

Computed tomography colonography (CTC) typically uses a helical computed tomography scanner to obtain contiguous axial cross sections of the lower abdomen. It will be recognized that other imaging technologies may be used instead of helical computed tomography, such as electron beam CT, magnetic resonance imaging (MRI), positron emission tomography (PET), or soft x-rays or high-resolution ultrasound. Because of the nature of CT data, typically seventy five to five hundred images are produced for a single series. The present invention provides an efficient way to handle the large number of images, reduce the amount of time required for diagnosis, and improve the reliability of the interpretation.

A preferred method of performing a CTC examination involves four sub-processes: 1) preparation of the colon, 2) scanning the colon, 3) identification of the colon midline, and 4) support of diagnostic interpretation by a radiologist. Dividing analysis steps into separate sub-processes is a significant departure from the paradigm of most medical imaging workstations. Current workstations, like most personal computer and workstation packages, typically are based upon a "toolbox" metaphor. The operator of these systems, like a craftsman in a work shop or an artist in a studio, has access to all of the tools and raw materials required to construct a finished product, which is in this case a medical diagnosis. The choice of tools and the order of their use are controlled by the operator. Given enough time, a skilled artist can construct a wide variety of finished products. However, the artist is not optimally efficient and would typically find it difficult to produce several identical products.

In contrast, the present invention provides for the users of CTC systems to operate in a manner similar to assembly line workers. Each receives intermediate results from a previous subsystem, performs a limited number of well-defined tasks, has access to the tools appropriate for the performance of these tasks, and passes the partially finished product on to the next stage in a well-defined state of completeness. Just as assembly lines are more efficient than craftsman, systems based upon the present invention's "pipeline" metaphor are often more efficient than those based upon the "toolbox" metaphor. Additionally, the present invention insures that the same processing steps are performed on each image data set, making it much more appropriate for scientific applications.

Figure 3:
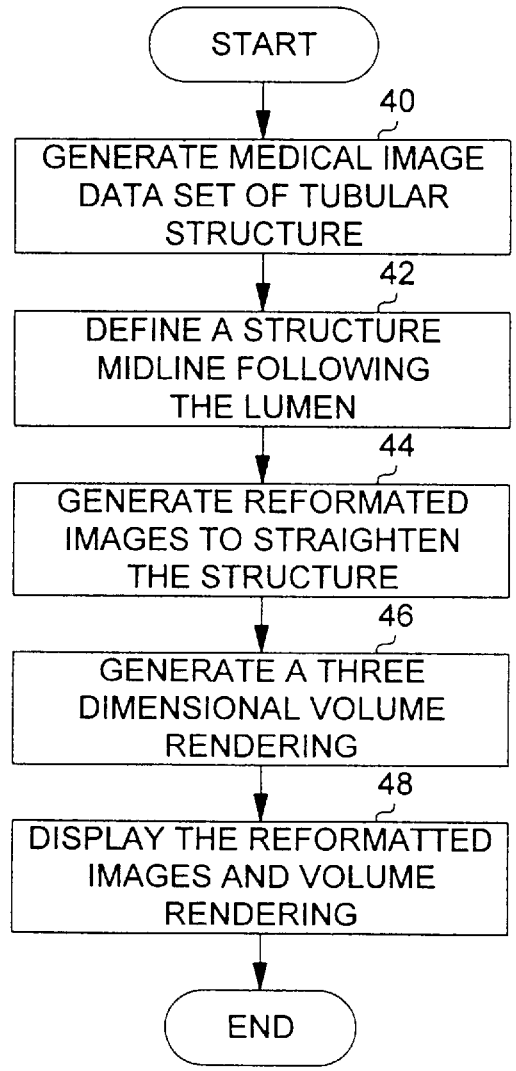
FIG. 3 is a flow diagram illustrating a method for imaging a human body with a medical imaging device compatible with the present invention.

FIG. 3 is a flow diagram illustrating a method for imaging a human body with a medical imaging device compatible with the present invention. At block 40, the medical imaging device 26 is used to generate an image data set of the structure within the human body. At block 42, the image data set is used to assist in defining a midline following the structure lumen. The midline may be manually defined, or semiautomatic tools may assist the user in creating the midline. At block 44, the computer 12 uses the image data set to automatically generate two dimensional reformatted images of the structure centered on the structure midline. At block 46, the computer 12 automatically generates a three dimensional intraluminal image of the structure. At block 48, the two dimensional reformatted images and the three dimensional intraluminal image of the structure are dynamically simultaneously displayed to the user on the display device 14.

PROCESSING

As described above, the preferred method of performing a CTC examination can be divided into four sub-processes: 1) preparation of the colon, 2) scanning the colon, 3) identification of the colon midline, and 4) support of diagnostic interpretation by a radiologist. The first two sub-processes are generally known within the prior art, but are briefly described below because they are significant to understanding the subsequent steps. The remaining two sub-processes are described in detail below.

Process 1: Preparation of the Colon

Initially, the present invention provides for colon preparation equivalent to that of traditional colonoscopy including fasting and the oral administration of laxatives. The patient's colon is insufflated with air. It will be recognized that other colon preparations may be used with the present invention, such as insufflating the colon with a gas other than air, filling the colon with a liquid contrast medium, using an oral stool marker in either the prepped or unprepped colon, or eliminating insufflation or filling of the colon altogether. It will also be recognized that a modification of the colon preparation procedure should be accompanied by corresponding modifications to the image analysis steps described below, because the modification will likely change the appearance of the colon's inner surface in the medical images.

Process 2: Scanning the Colon

Scanning is preferably performed on a fast helical CT scanner. As noted above, other medical imaging technologies may be substituted for a fast helical CT scanner without loss of generality. This technology requires a volumetric data set that covers the entire structure. Although a variety of scanning protocols are used, a typical collimation of five millimeters (mm) and a typical pitch of 1–2 is used. If a table speed of five mm per second is used, ten centimeters can be scanned in a 20 second breath hold. Since the colon spans a thirty to fifty centimeter region of the lower abdomen, three or four breath holds are required. Results produced by the present invention will improve as the technological improvement of CT scanners provides for machines which are capable of scanning the entire colon in a single breath hold. A reconstruction interval of one to three mm is often used.

Process 3: Identification of the Colon Midline

Following the scanning step described above, the reconstructed images are transferred to a computer workstation for identification of the colon. The midline, or midline, of the colon is delineated through the use of special purpose three dimensional tracing software. This software contains a full complement of manual and semiautomatic tools. Since the purpose of this subsystem is only to map the colon midline, optimal quality images are not necessary. Therefore, the scan is subsampled to the resolution of the workstation used as the display device. A preferred voxel volume of approximately eight cubic mm and a preferred contrast resolution of eight data bits is used with one embodiment of the present invention, although it will be recognized that the voxel volume and contract resolution may each be substantially increased or decreased without loss of generality. By using the preferred voxel volume and contrast resolution, the amount of data which must be processed is typically reduced by approximately a factor of sixteen.

Figure 4:
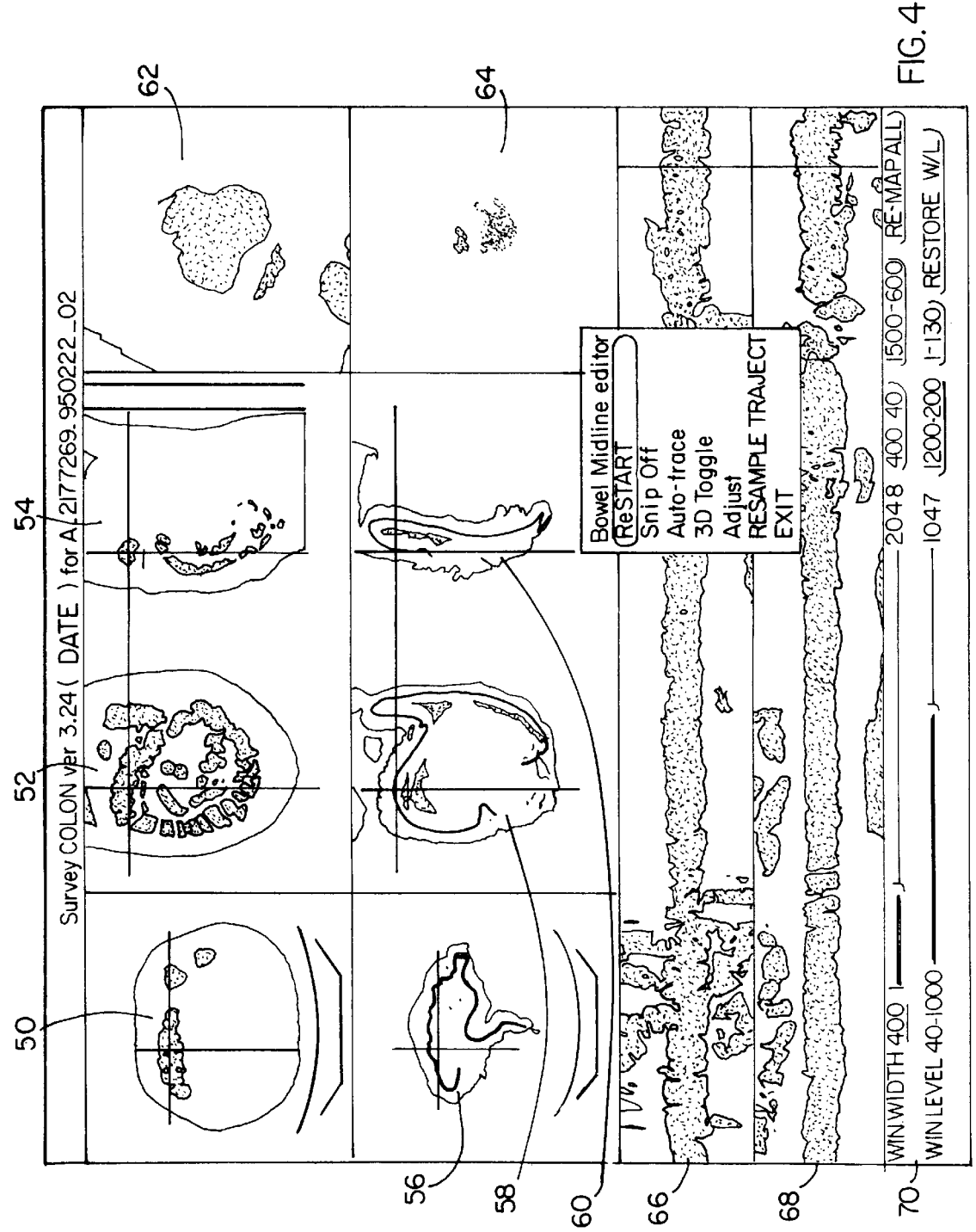
FIG. 4 is a screen display of a midline tracing tool used for semi-automatic tracing of a colon midline compatible with the present invention.

The computer workstation preferably displays images in a montage of views, including axial, coronal, and sagittal cross sections and corresponding rendered scout views, as shown in FIG. 4. Fiducial marks shown within each of the displayed views provide three dimensional localization. As the three dimensional course of the colon is delineated, the colon midline is preferably superimposed over the scout views and intersections with cross sections are displayed. Extension of the delineated midline or movement of the cursor in any image causes corresponding changes in the other images.

FIG. 4 illustrates a workstation display showing a preferred software interface of the present invention. The first three images on the upper row are axial 50, coronal 52, and sagittal 54 cross sections, respectively. Corresponding rendered scouts axial 56, coronal 58, and sagittal 60, are shown just below each of these views. The image 62 in the upper right portion of the display is an enlarged off axis cross section centered over the end of a delineated midline. Below this image is a low resolution rendered view 64 looking further into the colon. The elongated pictures at the bottom of the display 66, 68 are images of the straightened colon showing the entire length of the delineated colon. At the bottom of the display, a graphical user interface (GUI) control panel 70 allows a user to adjust the window and level settings. A pop-up window, not shown in FIG. 4, is used to access a tool kit of automatic tracing tools and similar options. Other windows, such as a parameter adjustment window, shown in FIG. 8, are used to adjust other settings and parameters within the system.

The preferred reduced scouts are depth shaded views of all intra-abdominal air. The rendering uses thresholding to identify the object to be rendered and very fast projection along cardinal directions. Depth buffers corresponding to each of these projections are also generated. These depth buffers are loaded with the average of the front surface coordinate and the first back surface coordinate. The buffers are used to determine three dimensional coordinates when a point is selected on one of the scouts. This feature simplifies pointing at the center of the colon.

Once the tracing of the colon midline has begun, four additional images are preferably displayed, as shown in FIG. 4. The first two images include 1) an off-axis cross section that is centered on the midline's endpoint and orthogonal to its final segment, and 2) a depth shaded intraluminal perspective volume rendered view from and aligned with the midline's endpoint.

The remaining two images are an innovative improvement of the "curved section" displays in well-known prior art medical imaging workstations. In conventional curved section displays, one axis is kept parallel to one cardinal direction in the scanned volume while the other tracks the specifying curve in the other two directions. The orthogonal pair of neo-curved sections included in the colon tracing subsystem of the present invention adapts to the extreme tortuosity of the colon and displays the identified midline as a straight line bisecting the displays. Each column of displayed imagery is preferably taken from along a line orthogonal to the colon midline in the scanned volume.

Manual Delineation of the Colon Midline

The midline can be identified manually in several ways. In a first method, coordinates can be identified by selecting a position in any of the scout views, shown in FIG. 4. Since the present invention automatically finds a point near the center of the colon, this is a quick and easy way to trace the colon. When the course of the colon is very tortuous, or the desired segment is obscured by other anatomy, the point identified may not correspond to the desired depth. In these cases, points can be selected in the reformatted 2D images.

A second effective method for extending the midline is to enter new points along the segment of the neo-curved sectional images which are beyond the current endpoint. Since the two views are orthogonal, alternately selecting new points in these two views can be used to extend the midline while keeping it centered in the colon.

It will be noted that the off-axis cross section is centered on the midline. Thus, the section will typically show a cross section of the colon that is centered on the image and is nearly circular. When points are entered in this image, the midline's endpoint is adjusted rather than extended. The image is therefore an effective tool for keeping the midline centered on the colon lumen.

Figure 5:
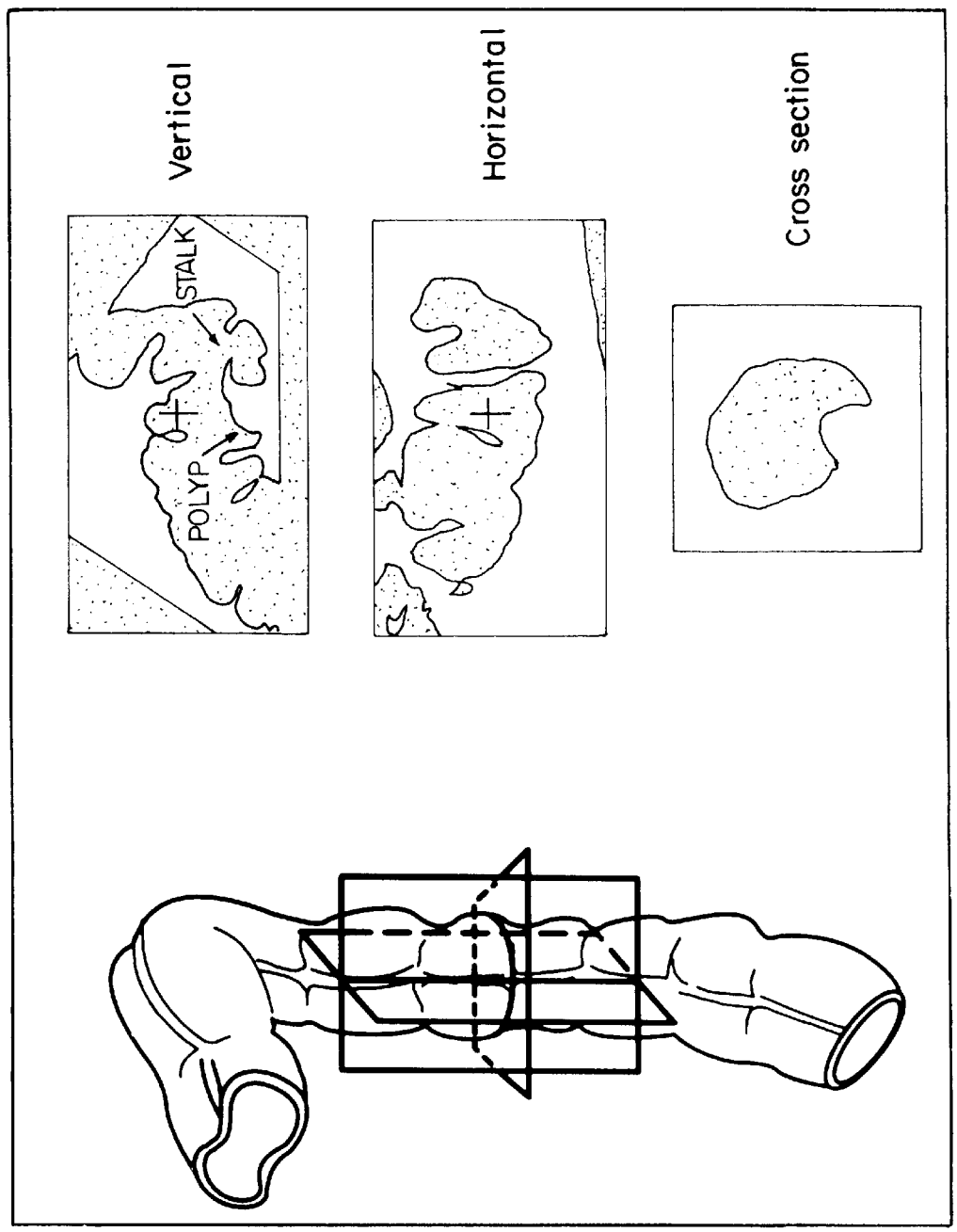
FIG. 5 is a screen display of cross section and orthogonal views to the colon centerline in a patient with a pedunculated polyp compatible with the present invention.
Figure 6:
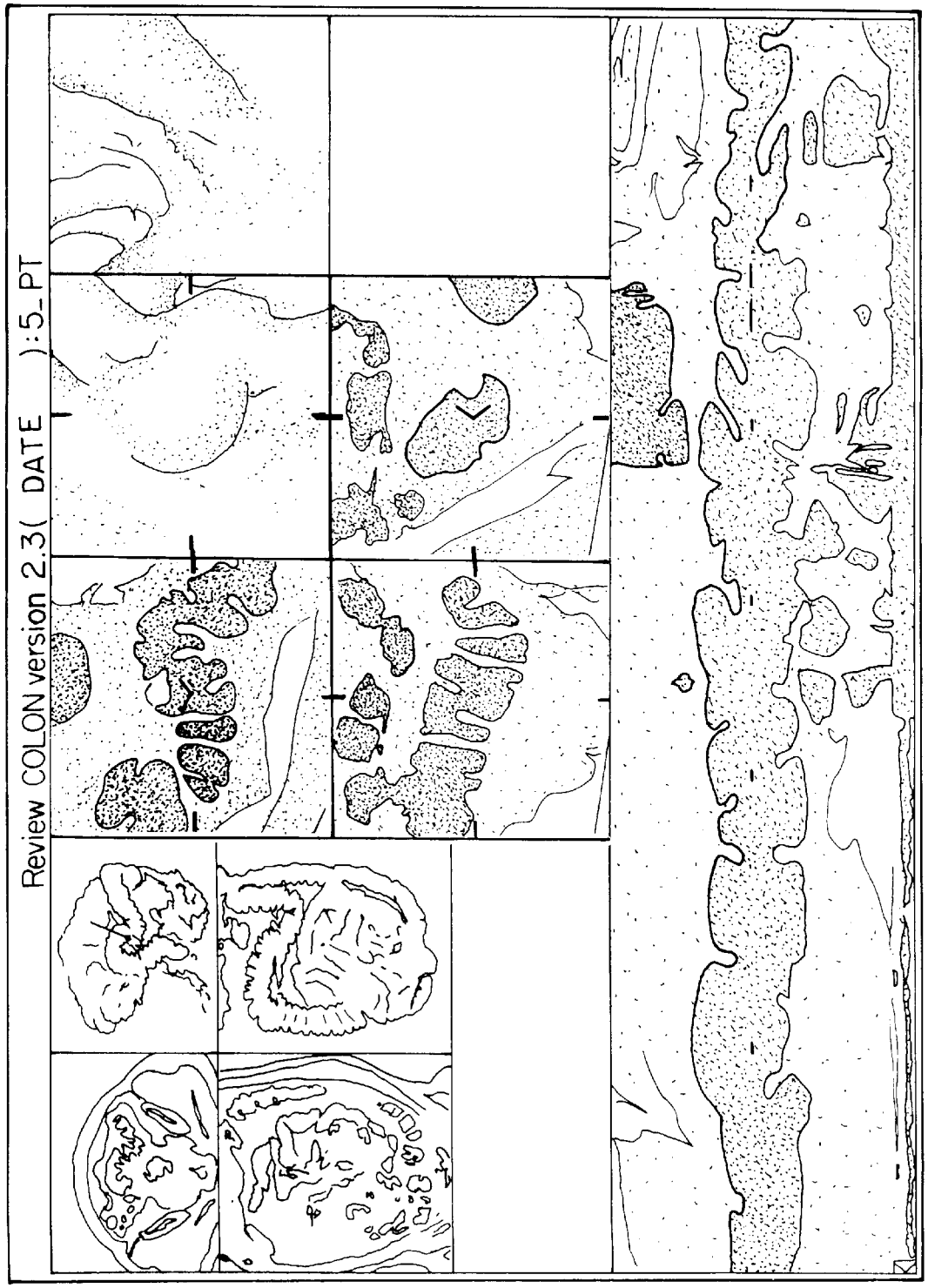
FIG. 6 is a screen display of a diagnostic image collage compatible with the present invention.

Ten images are produced to facilitate centerline definition: 2D axial and reformatted coronal and sagittal images as shown in FIG. 5, 3D extraluminal renderings in axial, coronal and sagittal views as shown in FIG. 6, a mathematically straightened colon in coronal and sagittal orientations as shown in FIGS. 4 and 6; and a 2D cross section and a 3D interluminal view as shown in FIGS. 4 and 6. The observer begins at the anal verge and advances through the colon until reaching the cecum using any of the ten displayed images. The orientation of the midline can be ascertained using the 2D cross section or 3D intra luminal views, and can be adjusted by the observer on these images. The observer may remove any preceding step as needed by using the keyboard and can then resume tracing from the last correct point.

The mathematically straightened views of the colon greatly facilitate midline delineation. Occasionally the path of the colon, especially in the sigmoid, may be difficult to define. In this case, the observer can use the 2D axial and reformatted coronal and sagittal images to determine the path of the sigmoid colon without interrupting the trace. The pointing device on the workstation, typically a mouse, allows the observer to scroll through 2D images in order to determine the path of the colon. Permanent trace points are placed using the pointing device.

Automatic Methods for Colon Midline Delineation

Several automated approaches to colon midline delineation are known within the prior art. A first approach is the "Marching Cubes" algorithm which finds the shortest path between two identified points which, as used in the subject matter of this invention, stays within the lumen of the colon. Since the start and end points must be specified, this can not truly be considered totally automatic. In addition, the algorithm is also computationally intensive. Further, the path found by the algorithm is the shortest and thus does not pass along the center of the colon. Instead, it will pass along the inner surface of each curve, which frequently results in obstructed views accompanied by disorienting abrupt changes in direction.

A second approach uses K-T transforms to find principal eigen vectors which track the course of the colon. This algorithm can only be applied where the radius of curvature of the colon midline is greater than twice the diameter of the colon. Virtually all colons fail to meet this criterion in at least one segment. Therefore, this algorithm is typically unreliable in the subject matter of the present invention.

A third approach would be to morphologically thin a binary volume image of the colon lumen into a single line and then vectorize the longest resulting path by a method similar to algorithms developed for analysis of remotely senses watersheds. While this approach is theoretically possible, there are no known prior-art implementations which are successful at tracing the colon. In addition, the algorithm would most likely be computationally intensive and may not resolve difficulties with highly convoluted segments.

In addition to the problems with the three automatic midline delineation approaches discussed above, none would be able to adapt to discontinuous shapes that are typically present in scans which are acquired in multiple breath holds or when bowel distention is lost. To adapt to these conditions, each of the above techniques must accept manual supervision and thus become semiautomatic. For any semiautomatic approach to be viable in clinical situations, it typically must be completely integrated with a manual system and must be able to perform the tracing faster than an operator of a totally manual system. These criteria are quite limiting for current workstation technology. Some or all of the above-mentioned approaches may be acceptable for limited research applications and may be found in future systems based upon higher performance computers.

Two Approaches to Midline Delineation

The present invention incorporates semiautomatic tools to facilitate midline delineation. These are designed to be faster than a supervising operator and to exploit features of the system which are included for manual operation. Each of these approaches finds an approximation of the colon midline.

A first approach extends the midline in the direction of its final segment a fixed fraction of the distance to the point where this line would pass out of the colon lumen. This point is known a priori because it is acquired by reading the central point of the depth shaded intra luminal view which is always present. An off-axis cross section is extracted at this new endpoint as described above. A two-dimensional region growing algorithm is used to find the center of the lumen on this cross section. The midline endpoint is iteratively adjusted until a satisfactory point is found. Then the midline is again extended in the direction of the last segment and the process is repeated. If a point is reached where the adjustment fails to converge, or the operator objects to direction of progress, processing is returned to manual control.

A second approach to semiautomatic tracing makes more direct use of the depth shaded intraluminal rendering. The centroid of the visible region of the colon lumen is calculated by applying a special case of Green's Theorem to the surface represented in the rendered image: If V is the volume bounded by a closed regular surface S, and if u(x,y,z) and v(x,y,z) are scalar functions having continuous second partial derivatives, then $$\iiint_V (u\nabla^2 v - v\nabla^2 u)dV = \iint_S N \cdot (u\nabla v - v\nabla u)dS$$

where N is the out normal to the surface S which bounds V.

The use of Green's Theorem makes this calculation very simple and is preferably embedded in the rendering software itself. This technique therefore requires little additional computation and is not iterative.

Midline Interpolation

Figure 7A:
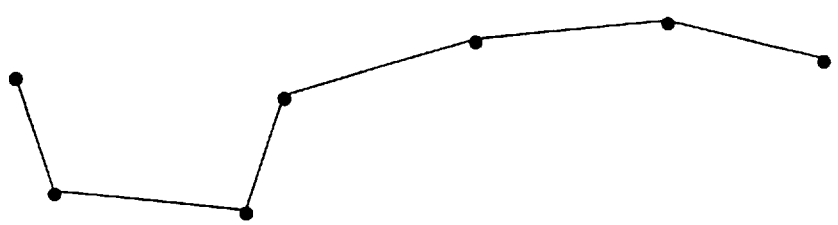
FIGS. 7a through 7c show the splining of a hypothetical midline by various algorithms.
Figure 7B:
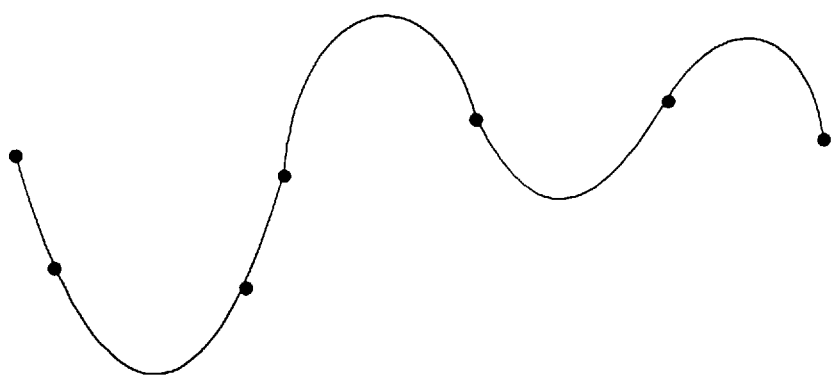

The traced colon midline is resampled to uniform length intervals. Various methods have been implemented and tested with the present invention. FIG. 7a illustrates a midline using linear splining, which results in abrupt changes in direction at each tie point. Cubic and parabolic splines were tried which yielded only approximately uniform sampling intervals and were often more erratic than was desirable, as shown in FIG. 7b. Second, a modified iterative parabolic spline and circular arc spline were used, which yielded uniformly spaced samples but also produced curves which were erratic. The problem with splines is that in passing through the data points, the splines are not smooth. Excessive curvature does not create excessive deviation of the line from a desired midline, but it does change the direction of the line sufficient to create an undesirable rocking of the perspective and off-axis views which are disorienting to the viewer and could potentially cause some small polyps to be missed.

Figure 7C:
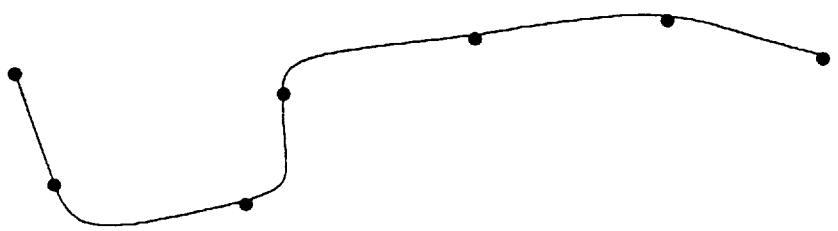

The present invention therefore preferably uses a circular arc and tangent interpolation method. As illustrated by FIG. 7c, an arc which is tangential to the current midline end segment and passes through the next point is determined. If the next point is behind the current endpoint, then a π radian arc and a connecting tangent are used. If the arc is between π/2 and π, a π/2 arc and a tangent line are used. If in any case the radius of the arc is less than 2 cm, the arc is sampled at π/16 radian increments. Otherwise, the sampling is fixed at 1 or 2 mm intervals along the colon. This method is shown by FIG. 4. An example of the excessive curvature generated by polynomial splines is shown in the center drawing. The same points are connected by the preferred arc and tangent spline in the lower drawing.

Process 4: Support of Diagnostic Interpretation

Upon completion of midline identification, the CTC scan is typically ready for diagnostic interpretation by a radiologist. This interpretation is supported by another application specific image manipulation tool. The radiologist preferably explores a colon by interacting with an intuitive user interface to navigate along the course of the colon. The manipulation tool presents a synchronous dynamic collage of reformatted 2D and rendered images. These images include navigational scouts, reformatted 2D cross sections, a 3D intraluminal image, and a straightened colon image which presents the entire length of the colon.

Interactive Navigation Tools

Two of the rendered views of intra-abdominal air, used for navigation in the earlier program described above, are also used to assist navigation. However, it is not necessary for the system to use depth maps to determine three dimensional coordinates. Instead, a point along the midline which is nearest to a projection of the selected position is determined, as shown in FIG. 4. This point is selected for the new view point and the corresponding reformatted 2D and 3D intraluminal images are displayed.

Positioning along the midline can also be controlled by selecting points in the reformatted 2D images themselves. As described above in FIG. 4, two of these cross sections are aligned with the colon midline. Selection of points away from the longitudinal center of these images causes the view point to move at an equivalent distance along the midline. In this way, the plane of the other cross section can be manipulated to traverse features seen in these images. This same method of selecting new view points can be used to rapidly scan a region of the colon. When points are iteratively selected at the same position on the screen, the view point progresses along the colon midline. The speed of this progress is determined by the distance between the selected point and the center of the view.

The position of the midline can also be controlled by selecting points along the straightened colon image described above. Generally, the length is too long to be displayed in its entirety on the workstation's screen. Instead, a segment is displayed at full resolution while the entire strip is displayed at a fractional scale. The segment to be displayed and the active view point can be selected using the scaled down section. Thus, the scaled down section functions in an analogous way to a horizontal "elevator" control common on graphical user interfaces. The plane of this cross section in the volume image of the straightened colon corresponds to a convoluted ribbon which bisects the colon along its axis. The orientation of this cut plane relative to the axis of the colon can be altered. This is done by selecting position in the off-axis cross section which is orthogonal to the midline. When the orientation is altered, a line is displayed in this section along the intersection of the two sections. This line is also ruled so that radial sizes can be measured.

The present invention does not require that the view point be limited to the midline. Images can be rendered from any position by selecting a view point on the 2D reformatted images. In an embodiment of the present invention, by pointing the cursor and simultaneously pressing the "Shift" key on the keyboard, an observer can "jump" off the midline and all images, including 2D reformatted images, 3D intraluminal images, and the 2D axial image are updated to views corresponding to the designated position. A fiducial mark on all images identifies the new position. The observer can advance both forward and backward along the new path, or using the pointing device, return to the nearest point on the predetermined midline.

3D Intraluminal Image Display

A 3D intraluminal image view is rendered that roughly corresponds to the video images from colonoscopy. Several prior art investigations use only these rendered views, and as such this technique is known as "virtual colonoscopy". As described above, a variety of rendering methods have been examined for use with the present invention which support interactive reorientation. For these methods, the view direction is controlled by selection of points in the rendered image. This causes the scene to be re-rendered with the selected feature at the center of the view.

Additionally, the view direction is represented and can be controlled in the navigational scouts. A bold fiducial mark such as a dot marks the current view point in these projections. A line segment extending from this point in the direction of the center of the rendered view is also shown. By manipulating the orientation of this indicator in the rendered scout, the radiologist can control the view direction with clear external reference points.

The display software preferably displays six 2D images: a reformatted 2D image, two orthogonal images, a view of the entire straightened colon, an enlarged image of one section of the straightened colon, and the raw axial 2D image. Two views of the three dimensional intraluminal images are displayed to the medical practitioner. The first is a forward view, and the second is a "rear-view" image looking backwards. Displaying both views makes it less likely that a feature of interest will be obscured due to the topology of the colon. Two 3D extraluminal renderings of the colon are displayed in axial and coronal orientations.

Several interactive features are available, including window and level settings, orientation of the 3D camera angle, and zoom adjustment of the 3D camera. The observer can choose which area of the colon to inspect by choosing a point on the extraluminal renderings of the colon or on the two straightened images of the colon. A measurement in millimeters from the anal verge is also displayed. Another feature allows the observer to inspect the entire colon wall surface. Using the reformatted 2D image, the observer can choose a slice of the colon wall to display as the straightened image. By sequentially rotating the orientation of the slice in either a clockwise or counterclockwise direction, the entire colon wall can be evaluated.

An observer typically begins viewing in the anal verge and advances along the trace using the workstation keyboard. Images can be displayed in both forward and reverse order. Colon polyps and cancers can be detected on both 2D and 3D images. Unlike 3D images, 2D images allow assessment of the colon wall/soft tissue interface so that the depth of the colon cancer invasion or other extraluminal disease process can be assessed.

As images are displayed, a bold fiducial mark is placed in the corresponding location on the extraluminal images. In this way, the observer knows which areas of the colon have been inspected. If an abnormality is detected, its location can be determined using both the extraluminal images as well as the measure report in millimeters from the anal verge.

Data Rendering

The present invention reduces the amount of time spent examining a patent's image data set by utilizing a 3D rendering technique that facilitates fast interactive evaluation of the image data set. In the known prior art, two types of data rendering are typically used to display 3D images views of the colon. The first type is surface rendering and the second type is volume rendering.

Surface rendering relies on a pre-processing step, known as segmentation, to identify the inner or mucosal surface of the colon and represent it as a mesh of triangles. A rendered view of the colon can then be generated very quickly by projecting each of these triangles onto a plane representing the display.

Volume rendering works with the 3D array of densities which comprise a CT scan volume. Each element or voxel in the array is projected onto a plane to generate a two dimensional rendered display image. If the entire volume array is used, it is possible to depict CT density as translucence in the rendered scene.

The process typically involved with volume rendering may require the evaluation of over one hundred times as much data as surface rendering, so volume rendering is typically much slower than surface rendering. For example, to generate an average rendered scene, approximately 20 computations must be performed on each volume element. Given that a 300 slice CT scan may contain over 75 million voxels, rendering such a volume on a computer capable of performing 100 million useful operations per second would require approximately 15 seconds.

Although the volume covered by a CTC scan is approximately 40 liters, the portion of this volume which is visible in an endoluminal view is typically less than 400 ml. The rendering technique embodied in the present invention uses this fact to limit the amount of processing by only evaluating relevant data within the volume array.

Figure 9:
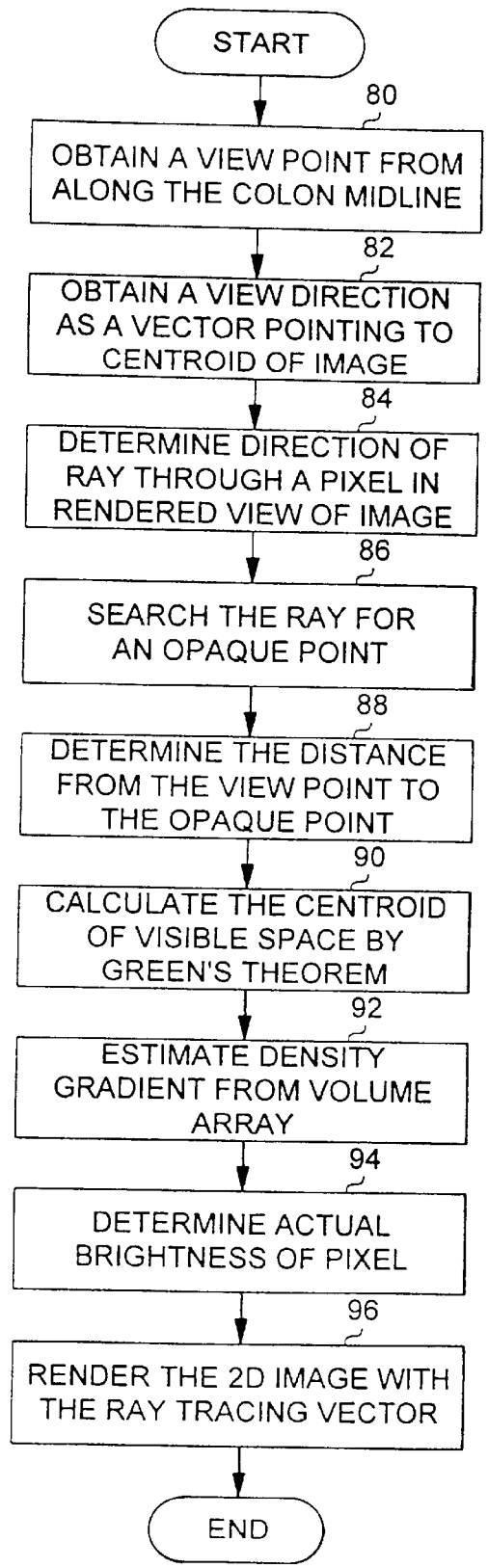
FIG. 9 is a flow diagram illustrating a method for rendering a 3D image compatible with the present invention.

FIG. 9 illustrates the preferred rendering method of the present invention. The rendering process of the present invention starts at block 80 by obtaining a view point within the volume array which is used as a virtual camera location. At block 82 a view direction is obtained which is used as the orientation direction of the virtual camera. The view point and view direction may be derived from along the colon midline, the centroid of the prior image rendering, or may be manually specified by the user. For each display point or pixel in the rendered view of the image, the rendering process determines the direction for a ray from the view point though the pixel at block 84. The ray is then cast along this direction through the volume array. At block 86, the ray is searched for an opaque point. The search is performed by sampling the volume array at uniform intervals along the ray. The interval is selected to coincide with the sample interval in the scan, allowing for the use of bilinear interpolation, instead of trilinear interpolation, which is typically used in volume rendering but requires nearly twice as many computer operations. At block 88, the exact distance from the view point to the opaque point on the ray is calculated by linear interpolation of the last two point values of the ray determined at block 86.

Block 88 results in the determination of a vector from the virtual camera to a point on the rendered surface. The centroid of the space visible in the rendered scene is preferably determined by applying Green's Theorem over the surface which is specified by the sum of all vectors determined at block 90. Rendered scenes which reflect the angle between the surface and the cast ray are preferred over simple depth shading. It is also desirable for the scene to reflect the density gradient along the cast ray. Estimating the density gradient is performed at block 92, where a density is preferably extracted from the volume array by trilinear interpolation to a point at a fixed distance beyond the opaque point on the array determined at block 88. The value of the fixed distance may be varied according to a "burrow depth" parameter, shown in FIG. 8. This enables an observer to manipulate the relative weighting of the two display properties, shading and density, described above. The actual brightness of a corresponding pixel in the rendered image is determined at block 94. The brightness of the pixel is determined as a linear combination of the density from block 92 and the distance from the view point to the opaque point on the ray from block 88.

Figure 10:
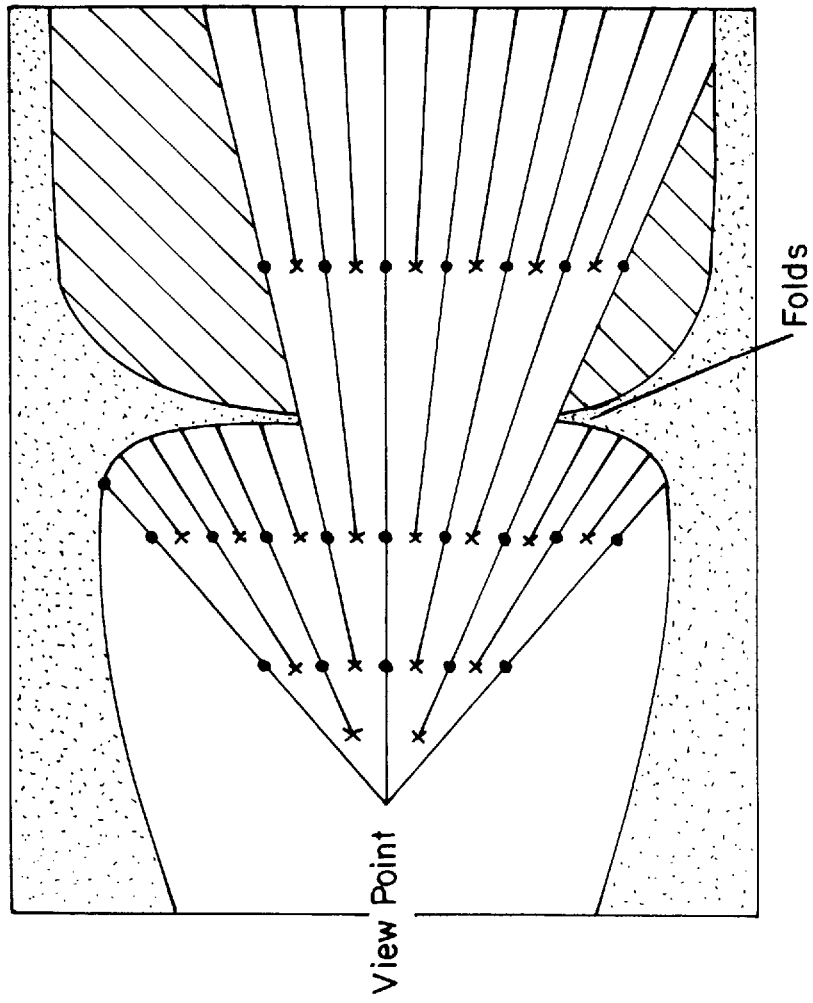
FIG. 10 is a schematic diagram illustrating a ray casting method compatible with the present invention.

In the preferred embodiment of the present invention, the steps shown in FIG. 9 are not all performed sequentially. Blocks 80 and 82 are performed selectively, then blocks 84 and 86 are performed for all pixels in the rendered scene. The processing loop for the earlier portion of this process is typically the most computationally intensive, but can be made more efficient by isolating it from the rest of the process steps. The process loop is performed at successfully higher resolutions and over progressively greater depth ranges. The start point for each ray in one iteration is determined from the result of the prior iteration, as shown schematically in FIG. 10.

Because the rendering of a 3D image stops when the racy tracing vector encounters the internal surface of the colon, a large amount of data which is not visible to the observer is eliminated, which greatly reduces the number of computations required to generate the ray traced image. This results in a volume rendering process with computational requirements similar to that of a surface rendering process. It will be recognized that the rendering technique of the present invention accommodates any view point along any view direction, and that a detected surface along the ray may represent structures other than the internal surface of the colon.

Opening the Colon

The present invention assists a medical practitioner with the diagnostic interpretation of medical images by displaying an unfolded or opened view of the colon. The opened view of the colon corresponds to a view of the entire colon as if it had been physically divided and opened for inspection. There are at least four methods for opening the colon.

The first method for opening the colon divides the colon in two along the planes of each of the longitudinal cross sections. This division creates a first half and a second half of the colon. An isometric volume rendering is then performed for two views of the colon, a view of the first half and a view of the second half, looking through the planes of each of the longitudinal cross sections. This process typically works best in segments where the colon is relatively straight, such as the ascending colon, descending colon, and possibly the transverse colon.

The second method for opening the colon divides the entire scan volume in two along a curved surface which passes through the colon midline and is parallel to one of the cardinal directions of the scan. As in the first opening method described above, an isometric volume rendering is then performed for the two views of the colon looking through the plane created by the division step.

A third method for opening the colon mathematically straightens the colon prior to sectioning, as in the first opening method described above. This straightening will typically distort the colon. However, the distortion will typically be less than is often seen in perspective views.

A fourth method for opening the colon involves distorting the colon such that rays projected from the straightened colon midline through the colon surface are represented as if they were parallel. As in the third opening method described above, this will further distort surface features of the colon, but may not necessarily adversely affect the readability of the colon rendering.

The present invention is to be limited only in accordance with the scope of the appended claims, since others skilled in the art may devise other embodiments still within the limits of the claims. In addition to perfecting CTC for colon screening, the present invention may also be applied to the examination of other tubular structures within the body. For example, at least the two dimensional aspects of the present invention may help evaluate aortic dissection and other CT angiography applications.

What is claimed is:

1. A method for imaging a tubular structure of a human body with a digital computer having a processor, a data input device, and a visual display device, the method comprising the steps of:
    (a) providing to the digital computer an image data set which is representative of the structure and generated by a medical imaging device;
    (b) generating with the processor and the image data set two dimensional reformatted images of the structure through a view point;
    (c) generating with the processor a three dimensional image of the internal anatomy of the structure at the view point; and
    (d) simultaneously displaying with the visual display device the corresponding two dimensional reformatted images and the three dimensional image of the structure at the view point.

2. The method of claim 1, further comprising a step of using the image data set to define a structure midline following the structure lumen.

3. The method of claim 2, wherein the two dimensional reformatted images of the structure are centered on the structure midline.

4. A method for imaging a tubular structure of a human body with a digital computer having a processor, a data input device, and a visual display device, the method comprising the steps of:
    (a) providing to the digital computer an image data set representative of the structure and generated by a medical imaging device;
    (b) generating with the processor and the image data set two dimensional reformatted images of the structure through a view point;

(c) generating with the processor a two dimensional axial image of the body, including the structure, at the view point; and (d) simultaneously displaying with the visual display device the corresponding two dimensional reformatted images and the two dimensional axial image of the structure at the view point.

5. A method for imaging a tubular structure of a human body with a digital computer having a processor, a data input device, and a visual display device, the method comprising the steps of:

(a) providing to the digital computer an image data set which is representative of the structure and generated by a medical imaging device;

(b) generating with the processor and the image data set two dimensional reformatted images of the structure through a view point;

(c) generating with the processor a two dimensional axial image of the body, including the structure, and a three dimensional image of the internal anatomy of the structure at the view point; and (d) simultaneously displaying with the visual display device the corresponding two dimensional reformatted images, and the two dimensional axial image and the three dimensional image of the structure at the view point.

6. The method of claim 3, wherein the medical imaging device comprises a helical scanning device and wherein an axis of rotation of the imaging device is substantially perpendicular to a longitudinal axis of the human body.

7. The method of claim 3, wherein the step of generating the image data set comprises a reconstruction interval of less than 10 millimeters.

8. The method of claim 3, wherein the step of displaying the three dimensional image of the structure comprises displaying the three dimensional image simultaneously in an axial view, a sagittal view, and a coronal view.

9. The method of claim 8, wherein the step of displaying the three dimensional image of the structure comprises displaying a distance value representing the distance from a first point located at an arbitrary location along the structure to a second point located at a terminating location of the structure.

10. The method of claim 3, wherein the step of displaying the two dimensional images comprises displaying the two dimensional images simultaneously in an axial view, a sagittal view, a coronal view, and a continuous orthogonal view along a straightened version of the structure.

11. The method of claim 3, wherein the step of defining the structure midline comprises manually defining a series of points along the structure lumen.

12. The method of claim 11, wherein the step of defining the structure midline following the structure lumen comprises generating a virtual spline passing through the series of points along the structure lumen, wherein the virtual spline is substantially parallel to the structure midline.

13. The method of claim 12, further comprising a step of displaying an intraluminal three dimensional view of the structure by generating a view point and a view direction with the structure midline such that a field of view defined by the view point and view direction substantially encompasses a view of the structure along the structure midline looking away from a terminating location of the structure.

14. The method of claim 12, further comprising the step of displaying an intraluminal three dimensional view of the structure by generating a view point and a view direction with the virtual spline such that a field of view defined by the view point and view direction substantially encompasses a view of the structure along the structure midline looking toward a terminating location of the structure.

15. The method of claim 12, further comprising the step of displaying an intraluminal three dimensional view of the structure by using a manually selected view point and a view direction which departs from the structure midline.

16. The method of claim 15, wherein the step of displaying an intraluminal three dimensional view of the structure by using a manually selected view point and a view direction comprises displaying a view of the structure forward and backward along a path defined by the manually selected view point and view direction.

17. The method of claim 16, wherein the step of displaying with the visual display device the two dimensional reformatted images and the three dimensional image of the structure comprises simultaneously dynamically updating the two dimensional reformatted images and three dimensional image forward and backward along the path defined by the manually selected view point and view direction.

18. The method of claim 3, wherein the step of displaying the three dimensional image of the structure comprises the steps of:

(a) obtaining a view point;

(b) defining a view direction as a vector pointing toward a centroid of one of the two dimensional reformatted images;

(c) casting a ray through the image data set from the view point along the view direction;

(d) determining a change in density point along the ray;

(e) projecting the ray past the change of density point; and (f) using the ray to display the three dimensional image of the structure.

19. The method of claim 3, wherein the step of displaying the three dimensional image of the structure comprises the steps of:

(a) defining the structure in a first half and a second half along a plane of longitudinal cross section of the structure; and (b) displaying the three dimensional image for a view of either the first or second half having a view direction through the plane of a longitudinal cross section of the structure.

20. A system for imaging a tubular structure of a human body with a digital computer having a processor, a data input device, and a visual display device, the system comprising:

(a) data transfer means for providing to the digital computer an image data set which is representative of the structure and generated by a medical imaging device;

(b) reformat means logically coupled to the digital computer for generating with the processor two dimensional reformatted images of the structure through a view point;

(c) render means logically coupled to the digital computer for generating with the processor a three dimensional image of the internal anatomy of the structure at the view point; and (d) display means logically coupled to the reformat means and render means for simultaneously displaying with the visual display device the corresponding two dimensional reformatted images and the three dimensional image of the structure at the view point.

21. The system of claim 20, further comprising definition means logically coupled to the digital computer for defining a structure midline following the structure lumen.

22. The system claim of 20, wherein the two dimensional reformatted images of the structure are centered on the structure midline.

23. A system for imaging a tubular structure of a human body with a digital computer having a processor, a data input device, and a visual display device, the system comprising:
(a) data transfer means for providing to the digital computer an image data set which is representative of the structure and generated by a medical imaging device;
(b) reformat means logically coupled to the digital computer for generating with the processor two dimensional reformatted images of the structure through a view point;
(c) render means logically coupled to the digital computer for generating with the processor a two dimensional axial image of the body, including the structure, at the view point; and
(d) display means logically coupled to the reformat means and render means for simultaneously displaying with the visual display device the corresponding two dimensional reformatted images and the two dimensional axial image of the structure at the view point.

24. A system for imaging a tubular structure of a human body with a digital computer having a processor, a data input device, and a visual display device, the system comprising:
(a) data transfer means for providing to the digital computer an image data set which is representative of the structure and generated by a medical imaging device;
(b) reformat means logically coupled to the digital computer for generating with the processor two dimensional reformatted images of the structure through a view point;
(c) render means logically coupled to the digital computer for generating with the processor a two dimensional axial image of the body, including the structure, and a three dimensional image of the internal anatomy of the structure at the view point; and
(d) display means logically coupled to the reformat means and render means for simultaneously displaying with the visual display device the corresponding two dimensional reformatted images, and the two dimensional axial and the three dimensional images of the structure at the view point.

25. The system of claim 22, wherein the medical imaging device comprises a helical scanning device and wherein an axis of rotation of the imaging device is substantially perpendicular to the longitudinal axis of the human body.

26. The system of claim 22, wherein the display means comprises a reconstruction interval in the range of between 1 and 10 millimeters.

27. The system of claim 22, wherein the display means comprises means for displaying the three dimensional image simultaneously in an axial view, a sagittal view, and a coronal view.

28. The system of claim 27, wherein the display means comprises means for displaying a distance value representing the distance from a first point located at an arbitrary location along the structure to a second point located at a terminating location of the structure.

29. The system of claim 22, wherein the display means comprises means for displaying the two dimensional reformatted images simultaneously in an axial view, a sagittal view, a coronal view, and a continuous orthogonal view along a straightened version of the structure.

30. The system of claim 22, wherein the definition means comprises manually defining a series of points along the structure lumen.

31. The system of claim 30, wherein the definition means comprises means for generating a virtual spline passing through the series of points along the structure lumen, wherein the virtual spline is substantially parallel to the structure midline.

32. The system of claim 31, wherein the display means comprises means for generating a view point and a view direction with the structure midline such that the field of view defined by the view point and view direction substantially encompasses a view of the structure along the structure midline looking away from a terminating location of the structure.

33. The system of claim 31, wherein the display means comprises means for generating a view point and a view direction with the virtual spline such that the field of view defined by the view point and view direction substantially encompasses a view of the structure along the structure midline looking toward a terminating location of the structure.

34. The system of claim 31, wherein the display means comprises means for displaying a three dimensional view of the structure by using a manually selected view point and a view direction which departs from the structure midline.

35. The system of claim 34, wherein the display means comprises means for displaying a view of the structure forward and backward along a path defined by the manually selected view point and view direction.

36. The system of claim 22, wherein the display means comprises means for simultaneously dynamically updating the two dimensional reformatted images and three dimensional image forward and backward along the path defined by the manually selected view point and view direction.

37. The system of claim 22, wherein the display means comprises means for simultaneously dynamically updating the two dimensional reformatted images and three dimensional image forward and backward along a path substantially parallel to the structure midline.

38. The system of claim 22, wherein the display means comprises:
(a) means for obtaining a view point;
(b) means for defining a view direction as a vector pointing toward a centroid of one of the two dimensional reformatted images;
(c) means for casting a ray through the image data set from the view point along the view direction;
(d) means for determining a change in density point along the ray;
(e) means for projecting the ray past the change of density point; and
(f) means for using the ray to display the three dimensional image of the structure.

39. The system of claim 22 wherein the display means comprises:
(a) means for defining the structure in a first half and a second half along a plane of longitudinal cross section of the structure; and
(b) means for displaying the three dimensional image for a view of either the first or second half having a view direction through the plane of the longitudinal cross section of the structure.

40. One or more program storage devices readable by a computer having a memory and coupled to a data storage device, each of the program storage devices including one or more programs of instructions executable by a computer to perform imaging of a tubular structure of a human body with a digital computer having a processor, a data input device, and a visual display device, the instructions including:

(a) first instruction means for enabling the digital computer to receive an image data set representative of the structure and generated by a medical imaging device;

(b) second instruction means for using the image data set to define a structure midline following the structure lumen;

(c) third instruction means for generating with the processor and the image data set two dimensional reformatted images of the structure through a view point centered on the structure midline;

(d) fourth instruction means for generating with the processor a three dimensional image of the internal anatomy of the structure at the view point; and (e) fifth instruction means for simultaneously displaying with the visual display device the corresponding two dimensional reformatted images and the three dimensional image of the structure at the view point.

41. A method for operating a digital computer system of the type having a processor, a visual display device and an operator-actuated input device to provide diagnostic images of a tubular structure of a human body at view points selected by a clinician through use of the operator-actuated input device, the method comprising the steps of:

receiving image data which is representative of the tubular body structure to be imaged;

generating from the image data, through each of a plurality of view points, a set of two dimensional reformatted images of the structure;

generating from the image data, at each of the view points, one or more additional images of the structure, the additional images being selected from a set of images including a two dimensional axial image of the body, including the structure, and a three dimensional image of the internal anatomy of the structure;

receiving information representative of the viewpoints selected by the operator through use of the operator-actuated input device; and simultaneously displaying on the visual display device the corresponding set of two dimensional reformatted images and each additional image of the structure at the selected viewpoints.

42. The method of claim 41 wherein:

the step of receiving information representative of viewpoints selected by the operator includes receiving information representative of a sequence of adjacent viewpoints along a navigated path of the structure; and the step of displaying the images includes updating the displayed images to simultaneously display the corresponding two dimensional reformatted images and each additional image of the structure at the adjacent viewpoints along the navigated path.

43. The method of claim 42 wherein the step of receiving information representative of viewpoints along a navigated path includes receiving information representative of viewpoints along a navigated path selected by a clinician through use of a mouse.

44. The method of claim 42 wherein the step of receiving information representative of viewpoints along a navigated path includes receiving information representative of viewpoints along a navigated path selected by a clinician through use of a keyboard.

45. The method of claim 41 wherein:

the step of receiving information representative of viewpoints selected by the operator includes receiving information representative of viewpoints along a midline of the structure; and the step of displaying the images includes displaying at least some of the corresponding images of the structure at the selected viewpoints along the structure midline.

46. The method of claim 41 wherein:

the step of receiving information representative of viewpoints selected by the operator includes receiving information representative of viewpoints off a midline of the structure; and the step of displaying the images includes displaying at least some of the corresponding images of the structure at the selected viewpoints off the midline of the structure.

47. The method of claim 46 and further including displaying a fiducial mark on at least one of the displayed images to identify the position of the viewpoint.

48. The method of claim 47 and further including displaying a mark on at least one of the displayed images to identify the direction of the viewpoint.

49. The method of claim 41 and further including displaying a fiducial mark on at least one of the displayed images to identify the position of the viewpoint.

50. The method of claim 41 and further including displaying a mark on at least one of the displayed images to identify the direction of the viewpoint.

51. The method of claim 41 wherein displaying the set of two dimensional reformatted images includes displaying two dimensional reformatted axial, sagittal and coronal views.

52. A method for operating a digital computer system of the type having a processor, a visual display device and an operator-actuated input device to provide diagnostic images of a tubular structure of a human body at view points selected through use of the operator-actuated input device, the method comprising the steps of:

receiving image data which is representative of the tubular body structure to be imaged;

generating from the image data, at each of the view points, a two dimensional axial image of the body including the tubular structure;

generating from the image data, through each of the view points, a set of two dimensional reformatted images of the tubular structure;

generating from the image data, at each of the view points, a three dimensional image of the internal anatomy of the tubular structure;

receiving information representative of viewpoints selected through use of the operator-actuated input device, including information representative of a sequence of adjacent viewpoints along a navigated path of the structure;

simultaneously displaying on the visual display device the corresponding two dimensional axial image, the set of two dimensional reformatted images and the three dimensional image at a selected viewpoint; and updating the visual display device to simultaneously display the corresponding images at the sequence of viewpoints along the navigated path of the structure.

53. The method of claim 52 wherein:

the step of receiving information representative of selected viewpoints includes receiving information representative of viewpoints along a midline of the structure; and the step of displaying the images includes displaying the set of two dimensional reformated images and the three dimensional endoluminal images of the structure at the selected viewpoints along the midline of the structure.

54. The method of claim 53 wherein:

the step of receiving information representative of selected viewpoints includes receiving information representative of viewpoints off a midline of the structure; and the step of displaying the images includes displaying the set of two dimensional reformatted images and the three dimensional endoluminal images of the structure at the selected viewpoints off the midline of the structure.

55. The method of claim 54 and further including displaying a fiducial mark on at least one of the displayed images to identify the position of the viewpoint.

56. The method of claim 55 and further including displaying a mark on at least one of the displayed images to identify the direction of the viewpoint.

57. The method of claim 56 wherein the step of receiving information representative of viewpoints along a navigated path includes receiving information representative of viewpoints along a navigated path selected through use of a mouse.

58. The method of claim 56 wherein the step of receiving information representative of viewpoints along a navigated path includes receiving information representative of viewpoints along a navigated path selected through use of a keyboard.

* * * * *